United States Patent
Helmer

(10) Patent No.: US 11,612,684 B2
(45) Date of Patent: Mar. 28, 2023

(54) ENCAPSULATION DEVICE, DRUG DELIVERY DEVICE AND EMERGENCY PACK

(71) Applicant: Sanofi-Aventis Deutschland GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 132 days.

(21) Appl. No.: 16/489,577

(22) PCT Filed: Feb. 26, 2018

(86) PCT No.: PCT/EP2018/054652
§ 371 (c)(1),
(2) Date: Aug. 28, 2019

(87) PCT Pub. No.: WO2018/158187
PCT Pub. Date: Sep. 7, 2018

(65) Prior Publication Data
US 2020/0009314 A1    Jan. 9, 2020

(30) Foreign Application Priority Data

Mar. 1, 2017    (EP) ..................................... 17158739

(51) Int. Cl.
*A61M 5/00*    (2006.01)
*A61M 5/20*    (2006.01)
*A61M 5/32*    (2006.01)

(52) U.S. Cl.
CPC .......... *A61M 5/002* (2013.01); *A61M 5/2033* (2013.01); *A61M 5/3204* (2013.01); *A61M 2205/584* (2013.01)

(58) Field of Classification Search
CPC .. A61M 5/002; A61M 5/3204; A61M 5/2033; A61M 2205/584; A61M 5/3129; A61M 5/3134; A61M 5/3135
(Continued)

(56) References Cited

U.S. PATENT DOCUMENTS

2014/0309591 A1* 10/2014 Holmqvist ............. A61M 5/24
                                                                  604/154
2016/0144132 A1    5/2016 Scanlon
2016/0193414 A1*  7/2016 Mcloughlin ........ A61M 5/5086
                                                                  604/227

FOREIGN PATENT DOCUMENTS

CN    101827621    9/2010
CN    102686255    9/2012
(Continued)

OTHER PUBLICATIONS

International Preliminary Report on Patentability in International Application No. PCT/EP2018/054652, dated Sep. 3, 2019, 11 pages.
(Continued)

*Primary Examiner* — Bhisma Mehta
*Assistant Examiner* — Nidah Hussain
(74) *Attorney, Agent, or Firm* — Fish & Richardson P.C.

(57) ABSTRACT

An encapsulation device for use with a drug delivery device comprises a housing containing a syringe, wherein the encapsulation device comprises at least: a body and a cap, wherein the body has an inner surface forming a cavity configured to retain an end of an outer surface of the housing of the drug delivery device, and the cap has an inner surface forming a cavity configured to retain the opposite end of the drug delivery device, and, in an assembled state of the encapsulation device, the cap and the body are releasably interconnected with each other to encapsulate the drug delivery device.

19 Claims, 6 Drawing Sheets

(58) Field of Classification Search
USPC .......................................................... 604/192
See application file for complete search history.

(56) References Cited

FOREIGN PATENT DOCUMENTS

| | | |
|---|---|---|
| CN | 103608055 | 2/2014 |
| CN | 105163782 | 12/2015 |
| CN | 105828851 | 8/2016 |
| JP | 2016-538078 | 12/2016 |
| KR | 10-1587235 | 1/2016 |
| KR | 10-1587238 | 1/2016 |
| WO | WO 2009/019437 | 2/2009 |
| WO | WO 2010/146358 | 12/2010 |
| WO | WO 2011/048223 | 4/2011 |
| WO | WO 2012/103140 | 8/2012 |
| WO | WO 2013/058697 | 4/2013 |
| WO | WO 2014/020001 | 2/2014 |
| WO | WO 2014/154498 | 10/2014 |
| WO | WO 2015/078758 | 6/2015 |
| WO | WO 2016/193341 | 12/2016 |
| WO | WO 2016/202916 | 12/2016 |
| WO | WO 2018/158187 | 9/2018 |

OTHER PUBLICATIONS

PCT International Search Report and Written Opinion in International Application No. PCT/EP2018/054652, dated May 7, 2018, 15 pages.

* cited by examiner

ENCAPSULATION DEVICE, DRUG DELIVERY DEVICE AND EMERGENCY PACK

CROSS-REFERENCE TO RELATED APPLICATIONS

The present application is a national stage entry of International Patent Application No. PCT/EP2018/054652, filed on Feb. 26, 2018, and claims priority to European Application No. 17158739.7, filed on Mar. 1, 2017, the disclosures of which are incorporated herein by reference.

TECHNICAL FIELD

The disclosure generally relates to an encapsulation device for use with a drug delivery device and to a drug delivery device. More particularly, the disclosure relates to an emergency pack.

BACKGROUND

Conventionally, drug delivery devices comprise a housing or a shell in a shape of a pen which holds a drug cartridge or a drug container or a pre-filled syringe. Some drugs, e.g. emergency drugs like glucagon, are required in small quantities and have special requirements for quickly finding and identifying them.

Thus, there is a need for an improvement for identifying if the drug delivery device contains a specific drug, in particular an emergency drug.

SUMMARY

The present disclosure meets the foregoing need by providing an encapsulation device for use with a drug delivery device.

The disclosure further provides an improved drug delivery device for use with e.g. an emergency drug to quickly find and identify the device.

The disclosure further provides an emergency medical pack for treatment of emergencies, in particular allergic emergencies.

Exemplary embodiments are provided in the dependent claims.

According to the disclosure, disclosed herein is an encapsulation device for use with a drug delivery device comprising a housing containing a syringe, wherein the encapsulation device comprises at least a body and a cap, wherein the body is configured to hold an end of the drug delivery device and the cap is configured to hold the opposite end of the drug delivery device and, in an assembled state of the encapsulation, the cap and the body are releasably interconnected with each other to encapsulate the drug delivery device.

In particular, the body has an inner surface forming a cavity configured to retain an end, e.g. a proximal end of an outer surface of the housing of the drug delivery device and the cap has an inner surface forming a cavity configured to retain the opposite end, e.g. a distal end of the drug delivery device.

The disclosure allows using known and usual drug delivery devices, in particular auto-injectors, for an emergency drug. No auto-injector or pen design changes are needed. Providing such an outer emergency cover or encapsulation device is easy and simple and very cost effective.

In some embodiments, the body is formed as a shell, in particular as an outer shell. The outer shell can individually change and is adapted to accommodate the drug delivery device so that no parts of the drug delivery device extend through the encapsulation device.

In some embodiments, the body and the cap are tightly closed in an assembled state. In particular, the assembled encapsulation device hermetically seals or tightly closes the drug delivery device. Additional seal members may be arranged between the cap and the body.

In some embodiments, the encapsulation device comprises a holder configured to be assembled onto the end, in particular a back end of the drug delivery device and to interconnect the body with this end, in particular the back end of the drug delivery device.

In some embodiments, the holder is a separate part from the body. According to an alternative embodiment the holder is formed on an inner side of the body. In particular the holder is integrated into the body wherein the holder and the body form a one-piece part.

In a further embodiment the holder has a cylindrical body which comprises a form and/or size corresponding to the form and size of the respective end, e.g. the back end of the drug delivery device. Furthermore, the holder is configured to releasably hold the back end of the drug delivery device. In particular, the holder comprises at least one flexible arm axially extending from the holder. For instance, the flexible arm comprises a fastener which is radially biased outwards or inwards. According to a possible embodiment the holder may comprise a flexible locking hook which is radially biased outwards or radially biased inwards.

In a further embodiment, the holder comprises two flexible arms longitudinally extending in opposite directions and configured to be locked into openings or windows in the outer surface of the housing in a friction-fit or force-fit manner. Due to the longitudinal extent of the flexible arms in opposite directions the holder may be fixed onto the outer surface of the housing of the drug delivery device in a backlash-free manner. In particular, the holder is coupled to the outer surface of the drug delivery device free of backlash in longitudinal direction.

In some implementations, the holder may comprise a further flexible arm longitudinally protruding from the holder and configured to be locked into recess, aperture or window in the inner surface of the body in a friction-fit or force-fit manner. The holder is arranged between the outer surface of the housing of the drug delivery device and the inner surface of the body of the encapsulation device. Due to the locking feature of the flexible arms of the holder, the holder retains the drug delivery device and the encapsulation device with respect to each other.

In some embodiments, the holder is configured as a clip being adapted to be brought into releasable clamping engagement with the outer surface of the housing. The shapes of the holder and outer surface may be such that the holder encircles the outer surface of the housing or a housing part to such an extent that locking and release prevention are created. In particular, the holder encircles a generally cylindrical or tube formed outer surface of housing or housing part to more than a half circle in cross-section as for a rings, sleeves, clamps, etc. Additionally locking structures of known kind, e.g. interlocking structures, hooks and eyes, pins and grooves, protrusions and undercuts, etc. may be provided on the holder or the outer surface of the housing.

According to a further embodiment, the encapsulation device comprises a cap remover coupled onto the cap. The cap remover may be a separate part from the cap. Alternatively, the cap and the cap remover are formed as a one-piece part. The cap remover allows an easy and fast decoupling of the cap from the body and, thus, an easy and fast opening of the encapsulation device to use the drug delivery device e.g. in an emergency case.

In a further embodiment, the cap and the cap remover are formed as separate parts which are connected to each other by at least one of a form-fit connection, a force-fit connection and a material bonded connection. In particular, the cap and the cap remover comprise corresponding crimp interfaces. Furthermore, the cap remover may comprise a grip. In some embodiments, the grip is formed as at least one of a gripping ring extending from the cap, a gripping material on the outer surface of the cap and a structured outer surface of the cap.

The disclosure provides a drug delivery device with an encapsulation device as described above. The drug delivery device is for instance an auto-injector, a pen-injector or a syringe.

The drug delivery device, in particular an auto-injector comprises a container containing the drug. Alternatively, the drug delivery device may comprise a cartridge or a syringe which is prefilled with the drug.

In some embodiments, the drug delivery device comprises a piston which slides inside the container to inject the drug. Additionally, the drug delivery device comprises actuator means for automatically injecting a patient with said drug.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. In some embodiments, a device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy sources. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against his or her body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (e.g., as typically found in an auto-injector) and a dose setting mechanism (e.g., as typically found in a pen-injector).

The disclosure further provides an emergency kit comprising a drug delivery device described above and an encapsulation device described above, wherein the drug delivery device is encapsulated by the encapsulation device. According to a further embodiment, an outer surface of the encapsulation device is configured in at least one parameter such that a specific drug contained within the drug delivery device may be quickly and easily identified by a person. In particular, the outer surface is colored, e.g. is colored in orange, red or yellow. Furthermore the outer surface may comprise a shape or form which allows a fast and easy identification of the specific drug contained within the drug delivery device. For instance, the outer surface may comprise a pen-shape.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
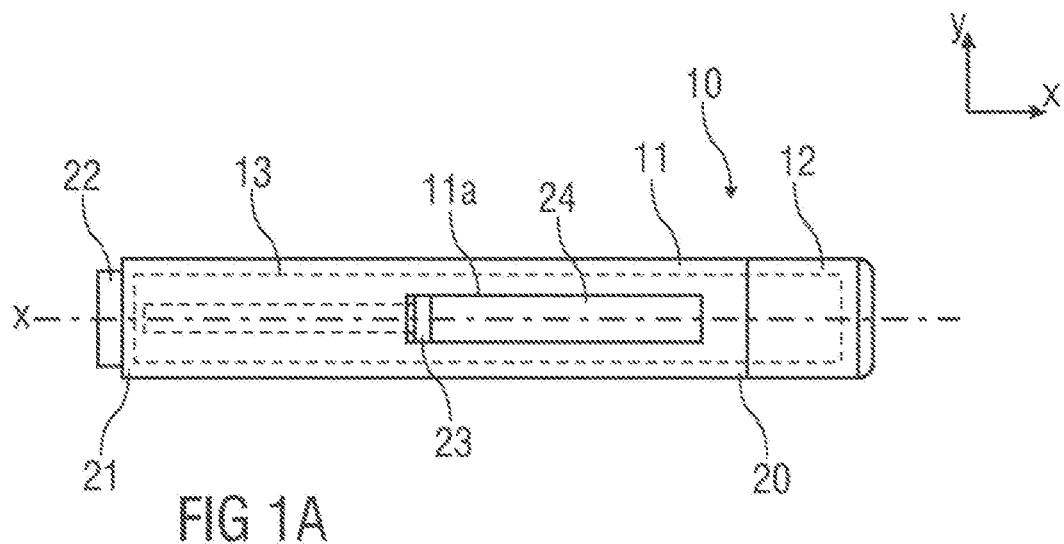
FIGS. 1A, 1B are schematic views of an embodiment of a drug delivery device without an encapsulation device.
Figure 1B:
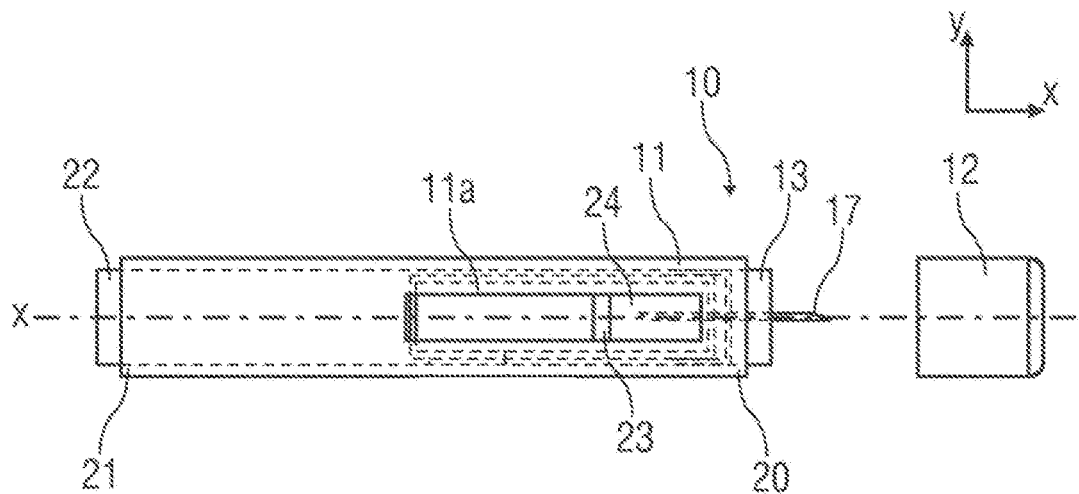

According to some embodiments of the present disclosure, an exemplary drug delivery device 10 is shown in FIGS. 1A and 1B.

Device 10, as described above, is configured to inject a medicament into a patient's body.

Device 10 includes a housing 11 which typically contains a reservoir containing the medicament to be injected (e.g., a syringe or a container) and the components required to facilitate one or more steps of the delivery process.

Device 10 can also include a cap assembly 12 that can be detachably mounted to the housing 11. Typically, a user must remove cap assembly 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal region 20 of housing 11.

Insertion of the needle 17 can occur via several mechanisms. For example, the needle 17 may be fixedly located relative to housing 11 and initially be located within an extended needle sleeve 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11.

Such insertion can be triggered by movement of sleeve 13 or by another form of activation, such as, for example, a button 22. As shown in FIGS. 1A & 1B, button 22 is located at a proximal end of the housing 11. However, in some embodiments, button 22 could be located on a side of housing 11.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the syringe 24 can be monitored.

Figure 2:
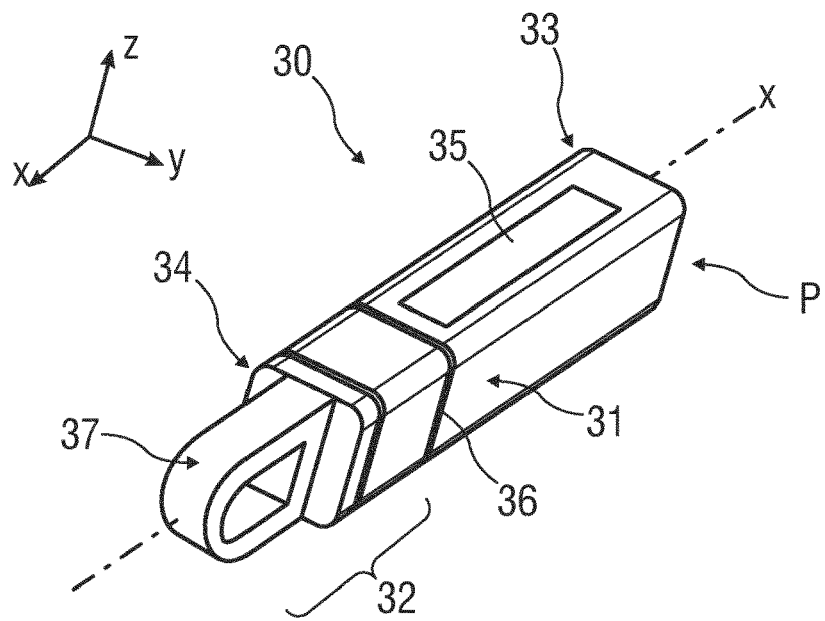
FIG. 2 is a schematic perspective view of an embodiment of an encapsulation device in an assembled or delivery state.

FIG. 2 is a schematic perspective view of an embodiment of an encapsulation device 30 in an assembled or delivery state.

The encapsulation device 30 is used in combination with a drug delivery device 10. The encapsulation device 30 comprises at least a body 31 and a cap 32. The body 31 is configured to hold a proximal region 21 of the drug delivery device 10. The cap 32 is configured to hold the opposite end, in particular a distal region 20 of the drug delivery device 10.

In an assembled state of the encapsulation device 30, the cap 32 and the body 31 are releasably interconnected with each other to encapsulate the drug delivery device 10, as shown in FIG. 2.

As illustrated, the encapsulation device 30 is substantially cylindrical and has a substantially constant diameter along the longitudinal axis X. Further, the encapsulation device 30 comprises a rectangular cross section. Alternatively, the encapsulation device 30 may comprise a round, circular or oval cross section. The encapsulation device 30 has a proximal portion 33 and a distal portion 34.

The encapsulation device 30 serves as an emergency medical pack P comprising a prefilled drug delivery device 10, e.g. a prefilled syringe in various styles with an emergency medical product or drug, e.g. epinephrine.

The encapsulation device 30 is for instance colored and labelled according to the emergency medical product. In particular, encapsulation device 30 comprises at least an identification portion 35, e.g. a window, recess or opening. This allows the user to immediately intuitively assess and locate the drug delivery device 10 with the specific emergency medical product without searching devices and medications. The disclosure allows using known and usual drug delivery devices 10, in particular auto-injectors in various styles, for emergency drugs.

The encapsulation device 30 is configured as strong lightweight outer housing. In particular, the body 31 is formed as an outer shell. The outer shell can individually change and is adapted to accommodate the drug delivery device 10 so that no parts of the drug delivery device 10 extend through the encapsulation device 30.

The body 31 and the cap 32 are tightly closed in an assembled state. In particular, the assembled encapsulation device 30 hermetically seals or tightly closes the drug delivery device 10. Further, the encapsulation device 30 is reinforced by e.g. reinforcement elements like inner ribs or reinforcement material like reinforced plastic, e.g. fiber-reinforced plastic. The encapsulation device 30 is impact-resistant and heat resistant. Hence, the drug delivery device 10 encapsulated by the encapsulation device 30 is protected against impacts, heat and/or fluids.

Each component or part, e.g. the cap 32 and the body 31 are conceivable depending on the usability needs. The body 31 as well as the cap 32 are configured as one of the easiest mouldable one-part solutions.

Additionally, a seal element 36, e.g. an O-ring seal or a flexible seal, may be arranged between the cap 32 and the body 31.

The encapsulation device 30 is designed to contain at least a drug delivery device 10, e.g. an auto-injector containing a pre-filled syringe 24, the body 31 (e.g. a shell), the cap 32 (e.g. a shell) and optionally a cap remover 37 (e.g. a de-capping aid), described below in more detail.

Figure 3:
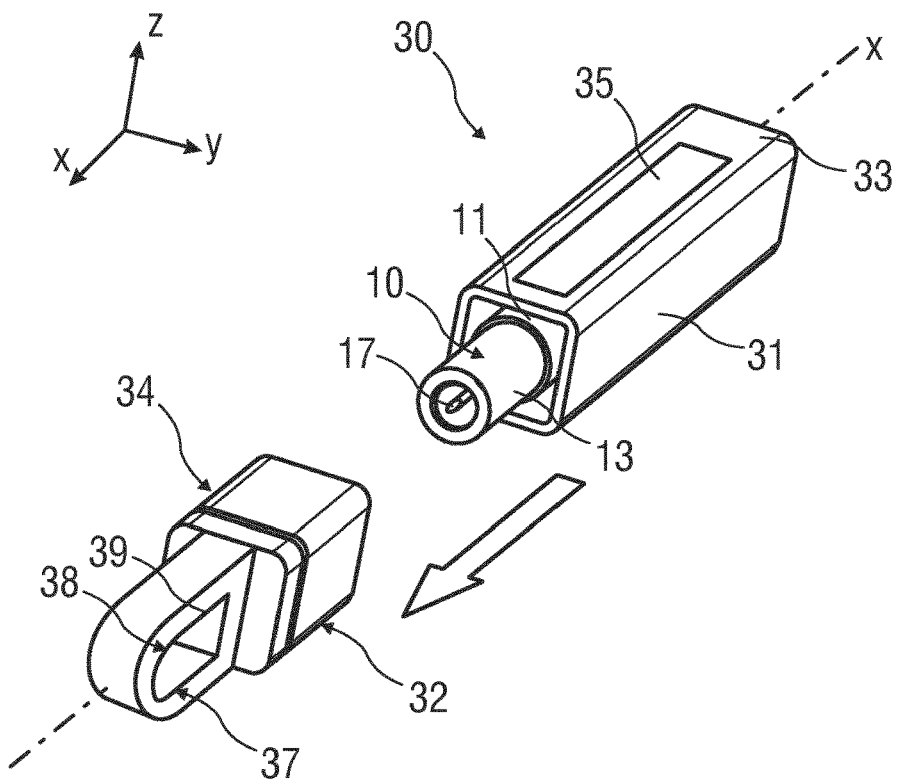
FIG. 3 is an exploded view of an encapsulation device.

FIG. 3 shows an exploded view of an encapsulation device 30. The outer cap 32 is detachably mounted to the body 31. Typically, a user removes the outer cap 32 from the body 31 before the drug delivery device 10 is removed or operated.

The outer cap 32 is for example configured to remove the cap assembly 12, e.g. a rigid needle shield (RNS shield) of the drug delivery device 10, too. The needle 17 of the de-capped encapsulation device 30 is further covered by the sleeve 13.

De-capping of the encapsulation device 30 can occur via several mechanisms. For example, the outer cap 32 may be removed alone from the body 31 and the cap assembly 12 may be subsequently removed from the drug delivery device 10. According to another example, due to coupling of the outer cap 32 with the inner cap assembly 12, the cap assembly 12 is simultaneously removable from the drug delivery device 10 while the outer cap 32 is removed from the body 31.

Furthermore, the cap 32 may comprise a cap remover 37. The cap remover 37 is configured to support easy removal of the cap 32 from the body 31.

In particular, the cap remover 37 may comprise a grip 38. The grip 38 is formed for example as a gripping ring 39 extending from the distal portion 34 of the cap 32. However, in some embodiments, the grip 38 may be configured as a gripping material on the outer surface of the cap 32 and/or as a structured, e.g. profiled outer surface of the cap 32. The cap 32 and the cap remover 37 are formed as a one-piece part, e.g. as a one-piece plastic part.

In some embodiments, the cap remover 37 is releasably coupled onto the cap 32. The cap remover 37 may be a separate part from the cap 32. The cap remover 37 allows an easy and fast decoupling of the cap 32 from the body 31 and, thus, an easy and fast opening of the encapsulation device 30 to use the drug delivery device 10, e.g., in an emergency case.

Figure 4:
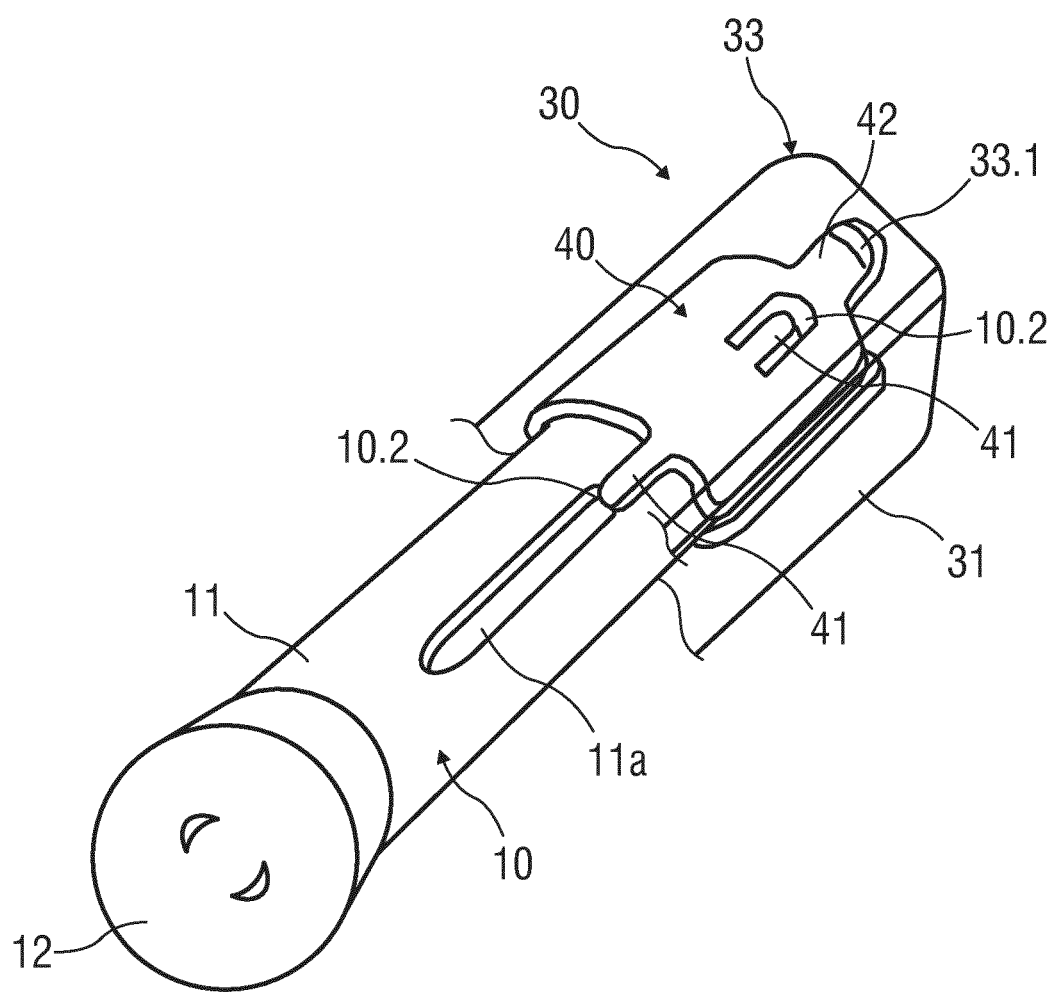
FIG. 4 is an enlarged exploded view of a distal portion of an encapsulation device.

FIG. 4 shows an enlarged exploded view of a distal portion 34 of an encapsulation device 30.

In some embodiments, the encapsulation device 30 comprises a holder 40. The holder 40 is configured to be assembled onto the end, in particular a back end of the drug delivery device 10. The holder 40 interconnects the proximal region 21 of the drug delivery device 10 with the proximal portion 33 of the body 31 of the encapsulation device 30.

In particular, the body 31 has an inner surface forming a cavity configured to retain the back end, e.g. a proximal end of an outer surface of the housing 11 of the drug delivery device 10. The cap 32 has an inner surface forming a cavity configured to retain the opposite end, e.g. a distal end of the drug delivery device 10.

In some embodiments, the holder 40 is a part separate from the body 31 and the drug delivery device 10. The holder 40 may be formed as a crimp part, e.g. a metal crimp, in particular as a slitted metal crimp. The holder 40 encompasses the proximal region 21 of the drug delivery device 10 (e.g. the auto-injector body). Such a holder 40 with a crimp mechanism allows a holding and fixation of the drug delivery device 10 by its crimp or clamp forces.

Figure 5:
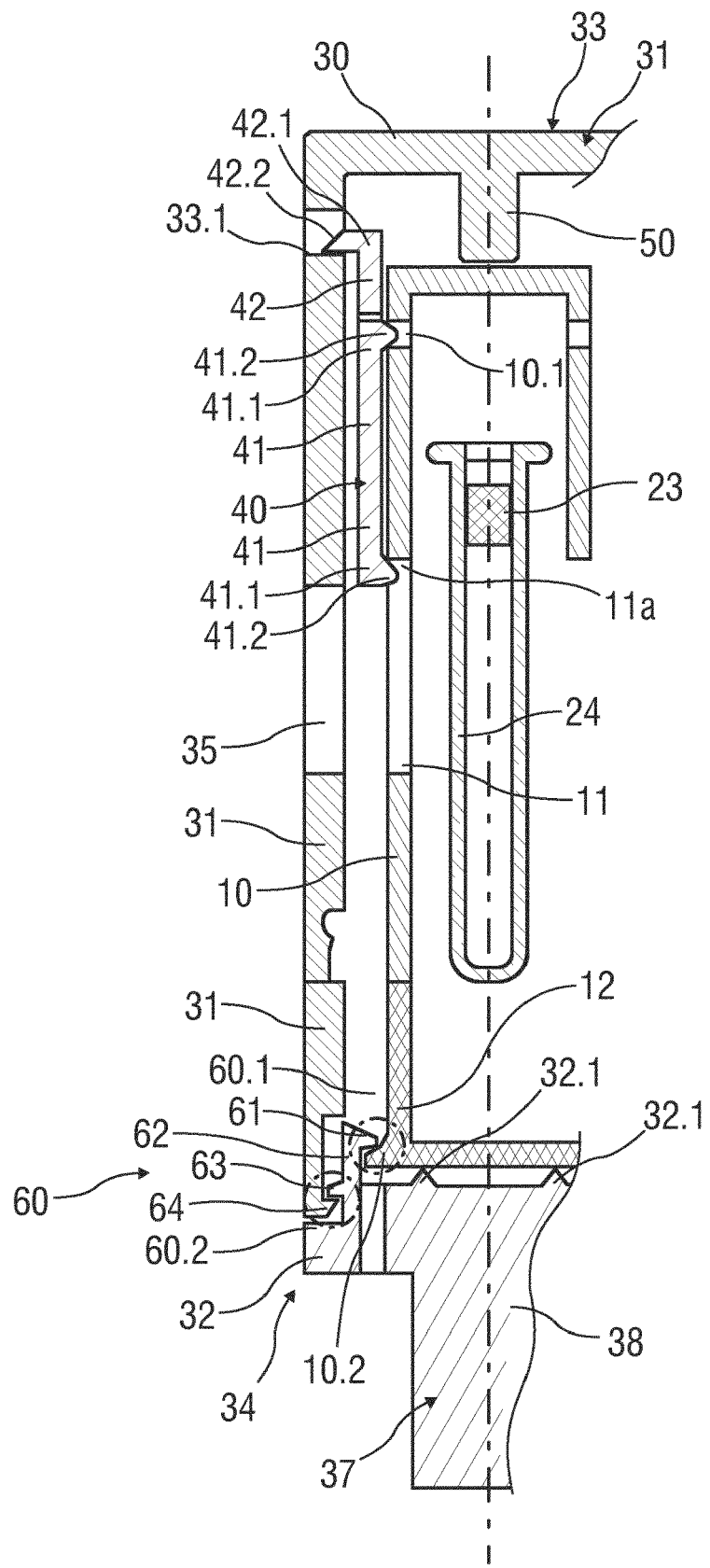
FIG. 5 is a sectional view of an encapsulation device with a drug delivery device.

FIG. 5 shows a sectional view of the encapsulation device 30 in an assembled state with an assembled drug delivery device 10.

The crimp mechanism comprises pins or hooks 41.2 and 42.2 that snap-in into pocket 10.1 and syringe window 11a of the housing 11 of the drug delivery device 10 and/or recess or opening 33.1. The hooks 41.2, 42.2 or pins eliminate free play tolerances between plastic components of the drug delivery device 10.

Further, the hooks 41.2, 42.2 may orientate the syringe window 11a of the drug delivery device 10 to the identification portion 35, e.g. a window or slot, in the body 31 of the encapsulation device 30. In an assembled state, the identification portion 35, e.g. a shell window, is aligned to the syringe window 11a of the drug delivery device 10.

In some embodiments, the holder 40 is formed on an inner side of the body 31. In particular, the holder 40 is integrated into the body 31 wherein the holder 40 and the body 31 form a one-piece part.

In some embodiments, the holder 40 has a cylindrical body. In particular, the holder 40 comprises a (inner) form, shape and/or size corresponding to the (outer) form, shape and size of the respective end, e.g. the back end of the drug delivery device 10. Furthermore, the holder 40 comprises a (outer) form, shape and/or size corresponding to the (inner) form, shape and size of the respective end, e.g. the proximal portion 33 of the body 31.

The holder 40 is configured to releasably hold and locate the back end (proximal region 21) of the drug delivery device 10. In particular, the holder 40 comprises one or more flexible arms 41 axially extending from the holder 40.

For instance, flexible arm 41 comprises fastener 41.1, e.g. locking hook 41.2 or snap interface which locks into the syringe window 11a and/or pocket/opening 10.1 of the drug delivery device 10. The flexible arm 41 may be radially biased outwards. In particular, the holder 40 comprises two flexible arms 41 longitudinally extending in opposite directions and configured to be locked into openings 10.1 and windows 11a in the outer surface of the housing 11 in a friction-fit or force-fit manner and backlash-free manner.

In some embodiments, the holder 40 is configured to releasably hold the proximal portion 33 of the encapsulation device 30. In particular, the holder 40 comprises one or more flexible holding arms 42 axially extending from the holder 40. The flexible arm 42 is configured to be locked into recess or window 33.1 in the inner surface of the body 31 in a friction-fit or force-fit manner. For instance, the flexible holding arm 42 comprises a snap fastener 42.1, e.g. locking hook 42.2 which locks into a corresponding locking opening 33.1 of the encapsulation device 30, in particular of the body 31. The flexible holding arm 42 may be radially biased inwards.

The shell recess or body opening 33.1 and the crimp snap-in feature of hook 42.2 in combination with the window 11a and the opening 10.1 and the crimp snap-in feature of hook 41.2 serve as a fixation of the drug delivery device 10 within the encapsulation device 30. Two or more snap-in mechanisms may be used for a perfect fitting and fixation.

In some embodiments, the encapsulation device 30 may comprise an end stop 50. The end stop 50 serves as an interface to the back end or proximal region 21 of the drug delivery device 10 during handling and assembly.

The cap 32 of the encapsulation device 30 and the cap assembly 12 of the drug delivery device 10 are formed as separate parts. The cap 32 and the cap assembly 12 are connected to each other by at least one of a form-fit connection and a force-fit connection. In particular, the cap 32 and the cap assembly 12 comprise corresponding crimp interfaces 60.

The crimp interfaces 60 are designed as several circumferential and/or separate snap mechanisms. The function of these crimp interfaces 60 is to hold the shell cap 32 in place with respect to the drug delivery device 10 before assembly of the shell body 31 onto the shell cap 32.

The shell cap 32 comprises for example snap hooks 61 arranged on flexible arms 62 which form a first snap-in connection 60.1. The snap hooks 61 extend inwards and engage and snap to a projection 10.2 of the drug delivery device 10. The snap hooks 61 in combination with the projection 10.2 serves as de-capping aid for the cap assembly 12 of the drug delivery device 10.

The shell cap 32 and the shell body 31 further comprise at the distal portion 34 of the encapsulation device 30 a second snap-in connection 60.2. The second snap-in connection 60.2 is a circumferential releasable connection. The second snap-in connection 60.2 comprises an outer projection 63 projecting outwardly from the shell cap 32 and an inner snap-in projection 64 projecting inwardly from the shell body 31. The second snap-in connection 60.2 serves as de-capping aid for the shell cap 32 of the encapsulation device 30.

The crimp interfaces or first/second snap-in connections 60.1, 60.2, in particular the combination of the two snap-in connections 60.1 and 60.2 serve for, while removing the outer shell cap 32, removing the inner cap assembly 12, too. The removing force has to be greater than the de-capping force of the drug delivery device 10 and smaller than the coupling force of the outer cap 32 and the inner cap assembly 12.

The cap 32 and the cap remover 37 are formed as a one-piece part. In some embodiments, the cap remover 37 and the cap 32 are separate parts that are connected to each other by at least one of a form-fit connection, a force-fit connection and a material bonded connection. In particular, the cap and the cap remover may comprise corresponding crimp or snap-in interfaces (not shown).

The drug delivery device 10 comprises a container or a pre-filled syringe 24 in which a piston 23 slides inside the syringe 24 to inject the drug. Additionally, the drug delivery device 10 comprises actuator means for automatically injecting a patient with said drug.

The outer shell cap 32 comprises ribs 32.1. The ribs 32.1 are formed on an inner side of the cap 32. The ribs 32.1 extend inwards. The ribs 32.1 prevent free-play between the cap 32 and the cap assembly 12.

In some embodiments, a radial crimp fixation and guiding arms are 90° shifted for an additional fixation of the outer shell cap 32 to the inner cap assembly 12.

Figure 6:
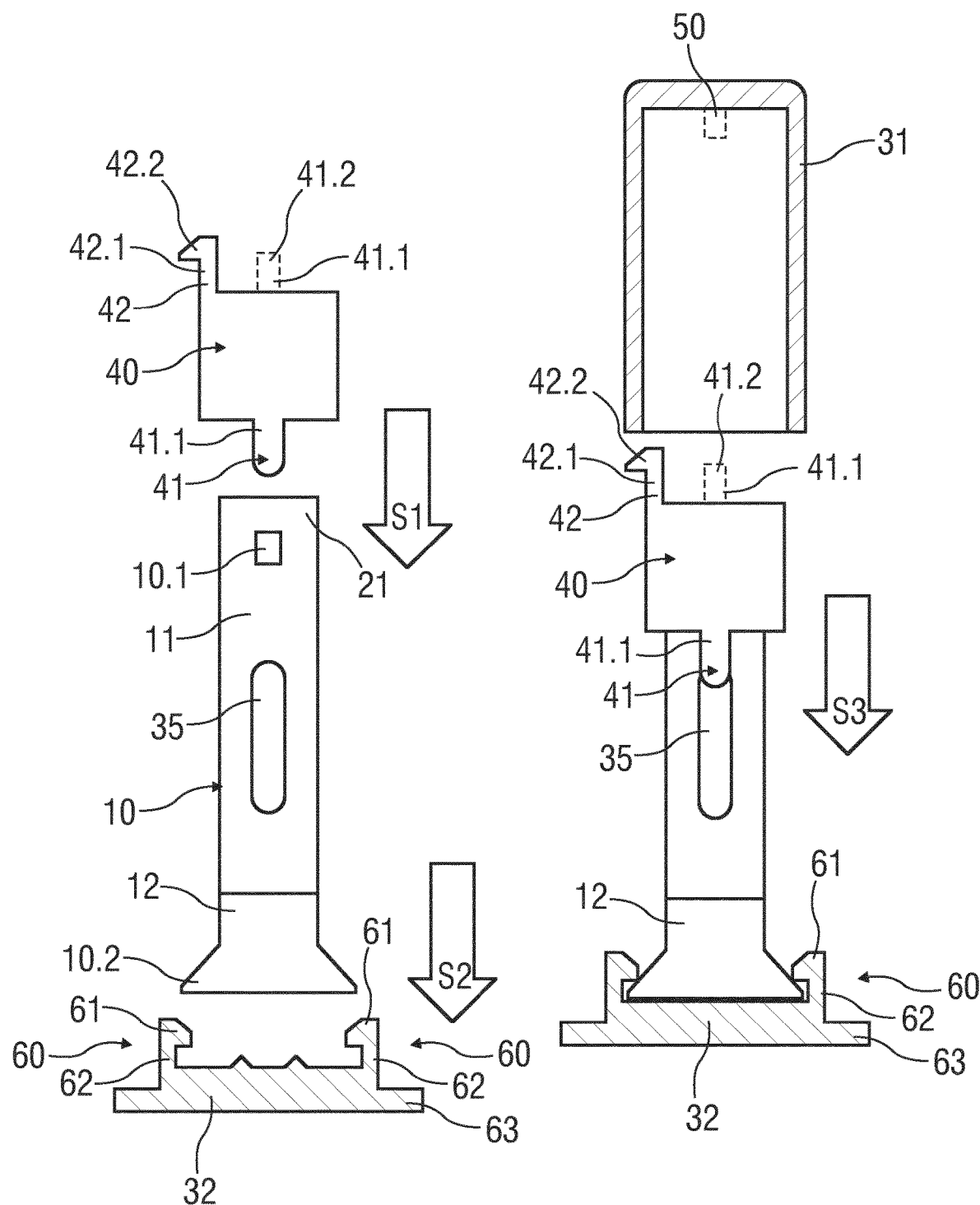
FIG. 6 is a schematic view of an embodiment for an assembling sequence of an encapsulation device.

FIG. 6 shows an embodiment for an assembling sequence of an encapsulation device 30. In a first step S1, the holder 40 is to be fixed onto the drug delivery device 10. In particular, the holder 40 is placed onto the proximal region 21 (back end) of the drug delivery device 10 until the locking hooks 41.2 lock into the window 11 a and the opening 10.1.

Subsequently, in a second step S2, the drug delivery device 10 is placed with its cap assembly 12 onto the outer shell cap 32 until the first snap-in connection 60.1 is locked. In a third step S3, the shell body 31 is placed onto the outer shell cap 32 until they lock with each other, for example by locking of the second snap-in connection 60.2 and by locking of the locking hook 42.2 into the shell opening 33.1.

In this final assembled state, the drug delivery device 10 is encapsulated by the encapsulation device 30 which form the emergency medical pack P shown in FIG. 1.

Figure 7:
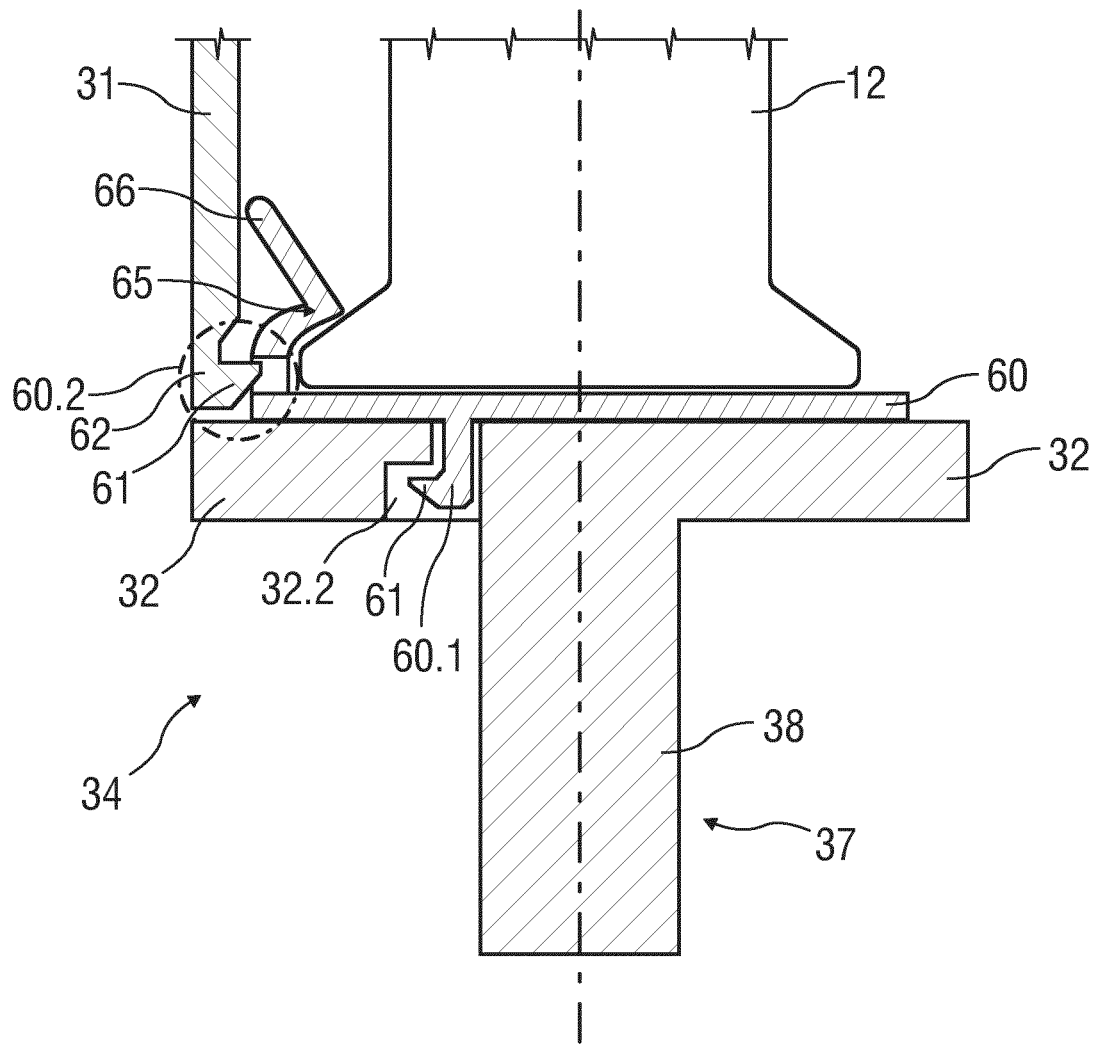
FIG. 7 is an enlarged sectional view of a proximal portion of an encapsulation device.

FIG. 7 shows an enlarged sectional view of an alternative embodiment of a distal portion 34 of the encapsulation device 30. For a better fixation of the cap assembly 12 to the outer shell cap 32, an additional support element 60 is provided. The support element 60 is formed as a metal part which could be arranged between the inner cap assembly 12 and the outer shell cap 32. The support element 60 could be fixed to the outer shell cap 32 by a first snap-in connection 60.1, e.g. a fitting element, a bayonet fitting or a snap-in hook 61, which locks into a cap recess 32.1.

When the drug delivery device 10 is assembled onto the outer shell cap 32, firstly, the support element 60 is arranged onto the outer shell cap 32 until the first snap-in connection 60.1 is locked. Subsequently, the cap assembly 12 is arranged onto the support element 60 and, thus, onto the outer shell cap 32. The support element 60 comprises a radial crimp or snap fixation 65. The crimp or snap fixation 65 comprises a holding arm 66 bent radially inwards, e.g. approximately 90° radially inwards for fixation of the outer shell cap 32 to the inner cap assembly 12 by the support element 60 and bent outwards, e.g. approximately 90° radially outwards for an additional fixation and securing of the coupling of the outer shell cap 32 and the cap assembly 12 during removing of the caps 12, 32.

Afterwards, the body 31 is assembled and arranged onto the outer shell cap 32 until the second snap-in connection 60.2 is locked. In this assembled state, the second snap-in connection 60.2 blocks the snap fixation 65. Thus, the snap fixation 65 is held in locking place.

While removing the outer shell cap 32, the second snap-in connection 60.2 is released. Due to the locked first snap-in connection 60.1 and the locked snap fixation 65, the cap assembly 12 is also removed. In particular, the holding arm 66 of the snap fixation 65 is held in locking place by the inner wall of the body 31 during removal until the holding arm 66 comes outside the body 31.

In summary, the disclosure provides a drug delivery device 10 with an encapsulation device 30 described above. The drug delivery device 10 is for instance an auto-injector, a pen-injector or a syringe.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES CHARACTERS 10 drug delivery device
10.1 pocket
10.2 projection
11 housing
11a window
12 cap assembly
13 needle sleeve
17 needle
17 distal region of the drug delivery device
20 proximal region of the drug delivery device
21 button
23 piston
24 syringe
30 encapsulation device
31 body
32 cap
32.1 rib
32.2 opening
33 proximal portion
33.1 opening
34 distal portion
35 identification portion
36 seal element
37 cap remover
38 grip
39 gripping ring
40 holder
41, 42 (flexible holding) arm
41.1, 42.1 fastener
41.2, 42.2 hooks
50 end stop
60 crimp interface
60.1 first snap-in connection
60.2 second snap-in connection
61 snap hooks
62 (flexible holding) arm
63 outer projection
64 inner snap-in projection
65 snap fixation
66 holding arm
P emergency medical pack
S1 to S3 assembling step
X longitudinal axis

The invention claimed is:

1. An encapsulation device for use with a drug delivery device, wherein the encapsulation device comprises:
a body that has an inner surface forming a cavity configured to retain an outer proximal end of a housing of the drug delivery device;
a cap that has an inner surface forming a cavity configured to retain an outer distal end of the drug delivery device, the outer distal end being opposite to the outer proximal end, wherein in an assembled state of the encapsulation device, the cap and the body are releasably interconnected with each other to encapsulate the drug delivery device; and
a holder configured to be assembled onto the outer proximal end of the housing of the drug delivery device to interconnect an inner end of the body with the outer proximal end of the housing of the drug delivery device, wherein the holder has a cylindrical body that comprises one or both of a form or a size corresponding to one or both of a form or a size of the respective end of the drug delivery device.

2. The encapsulation device according to claim 1, wherein the holder is a separate part from the body.

3. The encapsulation device according to claim 1, wherein the holder is formed on an inner side of the body.

4. The encapsulation device according to claim 1, wherein the holder comprises at least one flexible arm axially extending from the holder.

5. The encapsulation device according to claim 4, wherein the flexible arm comprises a fastener that is radially biased outwards or inwards.

6. The encapsulation device according to claim 1, wherein the holder comprises two flexible arms extending in opposite directions from the holder and configured to be locked into openings or windows in an outer surface of the housing in a friction-fit or force-fit manner.

7. The encapsulation device according to claim 1, wherein the holder comprises at least one flexible arm protruding from the holder and configured to be locked into a recess or window in the inner surface of the body in a friction-fit or force-fit manner.

8. The encapsulation device according to claim 1, wherein the holder is configured as a clip being adapted to be brought into releasable clamping engagement with an outer surface of the housing.

9. The encapsulation device according to claim 1, further comprising a cap remover coupled onto the cap.

10. The encapsulation device according to claim 9, wherein the cap and the cap remover are formed as one piece.

11. The encapsulation device according to claim 9, wherein the cap and the cap remover are formed as separate parts that are connected to each other by at least one of a form-fit connection, a force-fit connection, or a material bonded connection.

12. The encapsulation device according to claim 9, wherein one or both of: i) the cap and the cap remover comprise corresponding crimp interfaces, or ii) the cap remover comprises a grip.

13. The encapsulation device according to claim 12, wherein the grip is formed as at least one of a gripping ring extending from the cap, a gripping material on an outer surface of the cap, or a structured outer surface of the cap.

14. The encapsulation device according to claim 1, wherein a container or a syringe included in the housing of the drug delivery device is prefilled with a drug.

15. The encapsulation device according to claim 1, wherein a support element formed as a metal part is arranged between an inner cap assembly and the cap.

16. The encapsulation device according to claim 1, wherein the cap comprises snap hooks arranged on flexible arms forming a first snap-in connection, the snap hooks extending inwards to engage and snap to a projection of the drug delivery device.

17. An assembly comprising:
a drug delivery device configured to couple to an encapsulation device, the drug delivery device comprising an auto-injector or a pen-injector and a container or a syringe that is prefilled with a drug; and
the encapsulation device comprising:
a body,
a cap, and
a holder, wherein the body has an inner surface forming a cavity configured to retain an outer proximal end of a housing of the drug delivery device, the cap has an inner surface forming a cavity configured to retain an outer distal end of the drug delivery device, the outer distal end being opposite to the outer proximal end, wherein the holder is configured to be assembled onto the outer proximal end of the housing and to interconnect an inner end of the body with the outer proximal end of the housing, and in an assembled state of the encapsulation device, the cap and the body are releasably interconnected with each other to encapsulate the drug delivery device, wherein the holder has a cylindrical body that comprises one or both of a form or a size corresponding to one or both of a form or a size of the respective end of the drug delivery device.

18. An emergency pack comprising:
a drug delivery device; and
an encapsulation device comprising a body, a cap, and a holder, wherein the body has an inner surface forming a cavity configured to retain an outer proximal end of a housing of the drug delivery device, the cap has an inner surface forming a cavity configured to retain an outer distal end of the drug delivery device, the outer distal end being opposite to the outer proximal end, wherein the holder is configured to be assembled onto the outer proximal end of the housing and to interconnect an inner end of the body with the outer proximal end of the housing, and in an assembled state of the encapsulation device, the cap and the body are releasably interconnected with each other to encapsulate the drug delivery device, wherein the drug delivery device is hermetically encapsulated by the encapsulation device, and wherein a seal element is arranged between the cap and the body, wherein the holder has a cylindrical body that comprises one or both of a form or a size corresponding to one or both of a form or a size of the respective end of the drug delivery device.

19. A method of assembling an encapsulation device, the method comprising:
fixing a holder of the encapsulation device on a proximal region of a drug delivery device, the encapsulation device comprising a body and a cap, wherein the body has an inner surface forming a cavity configured to retain an outer proximal end of a housing of the drug delivery device, the cap comprising an inner surface forming a cavity configured to retain an outer distal end of the drug delivery device, the holder being configured to be assembled onto the outer proximal end of the housing and to interconnect an inner end of the body with the outer proximal end of the housing;
placing a cap assembly of the drug delivery device onto the cap, wherein in an assembled state of the encapsulation device, the cap and the body are releasably interconnected with each other to encapsulate the drug delivery device; and
placing the body onto the cap until the body and the cap lock each other.

* * * * *